(12) United States Patent
Mullaney et al.

(10) Patent No.: US 9,417,403 B2
(45) Date of Patent: Aug. 16, 2016

(54) FIBER OPTIC CONNECTOR WITH FIELD INSTALLABLE OUTER CONNECTOR HOUSING AND KEYED FERRULE HUB

(71) Applicant: CommScope Technologies LLC, Hickory, NC (US)

(72) Inventors: Julian S. Mullaney, Raleigh, NC (US); Eric Emmanuel Alston, Fuquay-Varina, NC (US); William Alan Carrico, Raleigh, NC (US)

(73) Assignee: CommScope Technologies LLC, Hickory, NC (US)

( * ) Notice: Subject to any disclaimer, the term of this patent is extended or adjusted under 35 U.S.C. 154(b) by 0 days.

(21) Appl. No.: 14/934,354

(22) Filed: Nov. 6, 2015

(65) Prior Publication Data

US 2016/0062053 A1    Mar. 3, 2016

Related U.S. Application Data

(63) Continuation of application No. 14/091,984, filed on Nov. 27, 2013, now Pat. No. 9,182,567.

(60) Provisional application No. 61/731,838, filed on Nov. 30, 2012.

(51) Int. Cl.
*G02B 6/38* (2006.01)
*G02B 6/46* (2006.01)

(52) U.S. Cl.
CPC ............ *G02B 6/3851* (2013.01); *G02B 6/3821* (2013.01); *G02B 6/3863* (2013.01); *G02B 6/3869* (2013.01); *G02B 6/3871* (2013.01); *G02B 6/3887* (2013.01); *G02B 6/46* (2013.01);

(Continued)

(58) Field of Classification Search
CPC .... G02B 6/3821; G02B 6/3869; G02B 6/387; G02B 6/3887; G02B 6/46; G02B 6/3851; G02B 6/3863; G02B 6/3871; Y10T 29/49826
USPC ................................................ 385/78, 85, 88
See application file for complete search history.

(56) References Cited

U.S. PATENT DOCUMENTS 5,212,752 A    5/1993    Stephenson et al.
5,809,192 A    9/1998    Manning et al.
(Continued)

FOREIGN PATENT DOCUMENTS

WO    WO 02/052310    7/2002
WO    WO 2008/091720    7/2008

OTHER PUBLICATIONS

International Search Report and Written Opinion for PCT/US2013/072018 mailed Mar. 25, 2014.

*Primary Examiner* — Akm Enayet Ullah
(74) *Attorney, Agent, or Firm* — Merchant & Gould P.C.

(57) ABSTRACT

An optical connector includes a first sub-assembly that is factory-installed to a first end of an optical fiber and a second sub-assembly that is field-installed to the first end of the optical fiber. The optical fiber and first sub-assembly can be routed through a structure (e.g., a building) prior to installation of the second sub-assembly. The second sub-assembly interlocks with the first sub-assembly to inhibit relative axial movement therebetween. Example first sub-assemblies include a ferrule, a hub, and a strain-relief sleeve that mount to an optical fiber. Example second sub-assemblies include a mounting block; and an outer connector housing forming a plug portion.

20 Claims, 7 Drawing Sheets

(52) U.S. Cl.
CPC ........... *G02B 6/387* (2013.01); *Y10T 29/49826* (2015.01)

(56) References Cited

U.S. PATENT DOCUMENTS

| | | | |
|---|---|---|---|
| 6,151,432 A | 11/2000 | Nakajima et al. | |
| 6,695,489 B2 | 2/2004 | Nault | |
| 6,913,392 B2 | 7/2005 | Grzegorzewska et al. | |
| 7,198,409 B2 * | 4/2007 | Smith | G02B 6/3849 385/53 |
| 7,510,335 B1 | 3/2009 | Su et al. | |
| 8,391,664 B2 | 3/2013 | Kowalczyk et al. | |
| 8,439,577 B2 | 5/2013 | Jenkins | |
| 8,548,293 B2 | 10/2013 | Kachmar | |
| 8,753,022 B2 | 6/2014 | Schroeder et al. | |
| 2003/0231839 A1 | 12/2003 | Chen et al. | |
| 2004/0023598 A1 * | 2/2004 | Zimmel | B24B 19/226 451/41 |
| 2005/0084215 A1 | 4/2005 | Grzegorzewska et al. | |
| 2007/0172173 A1 | 7/2007 | Adomeit et al. | |
| 2011/0176785 A1 | 7/2011 | Kowalczyk et al. | |
| 2015/0338582 A1 * | 11/2015 | Halls | G02B 6/245 425/510 |

* cited by examiner

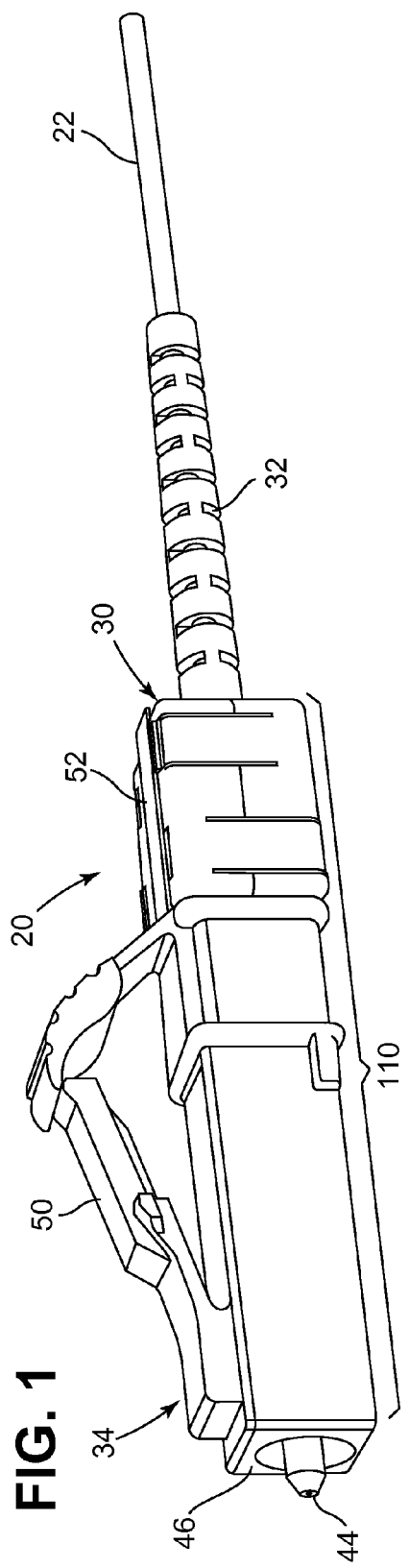
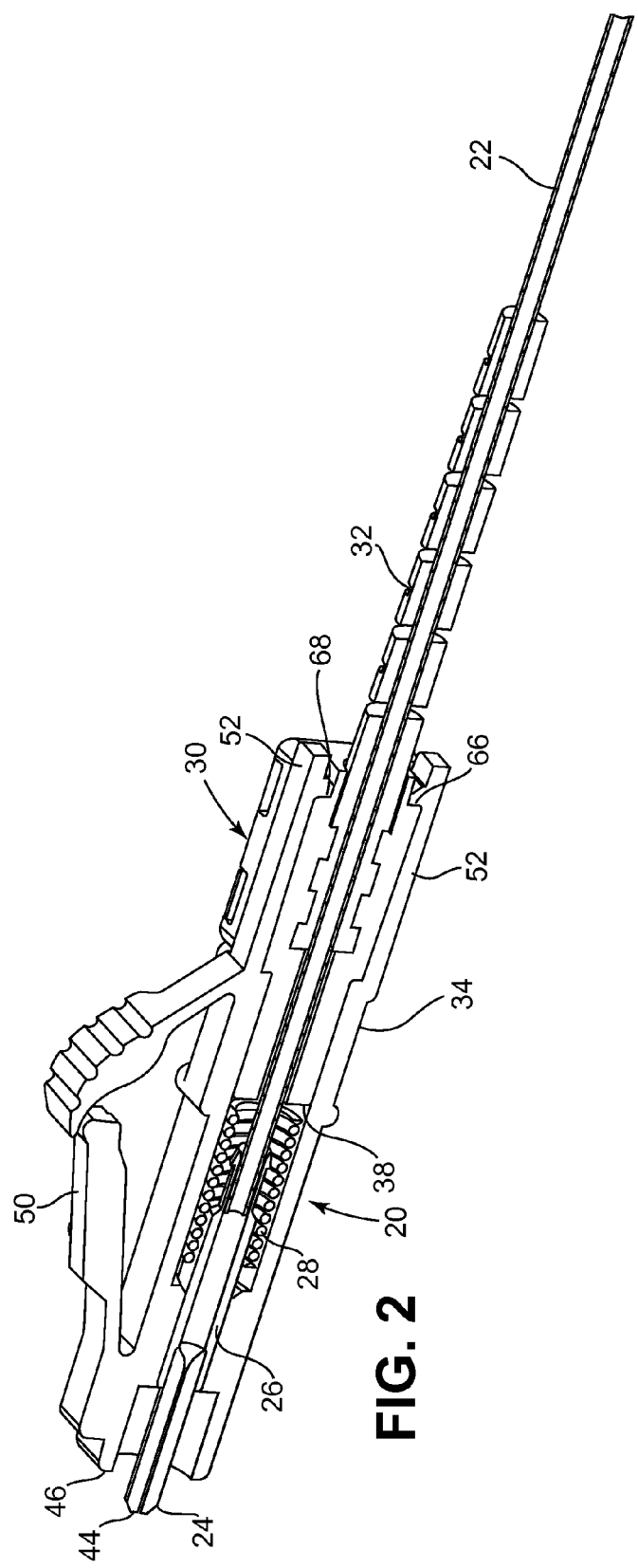
FIG. 1
FIG. 2

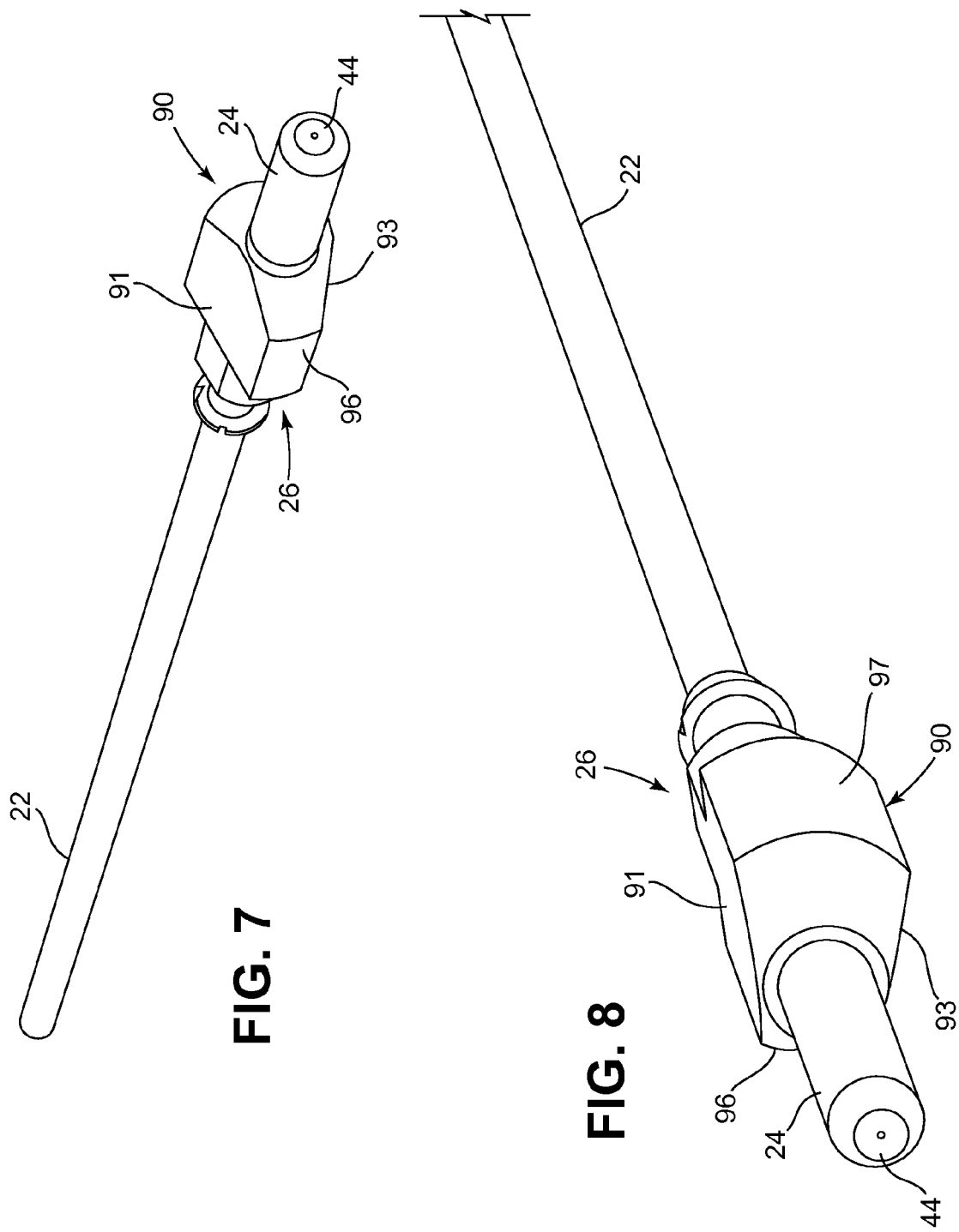

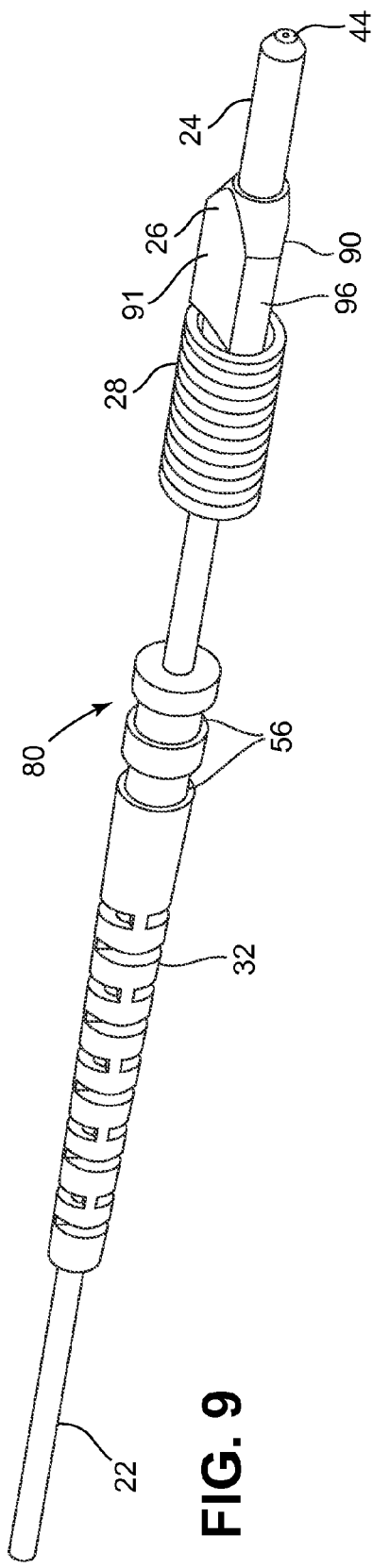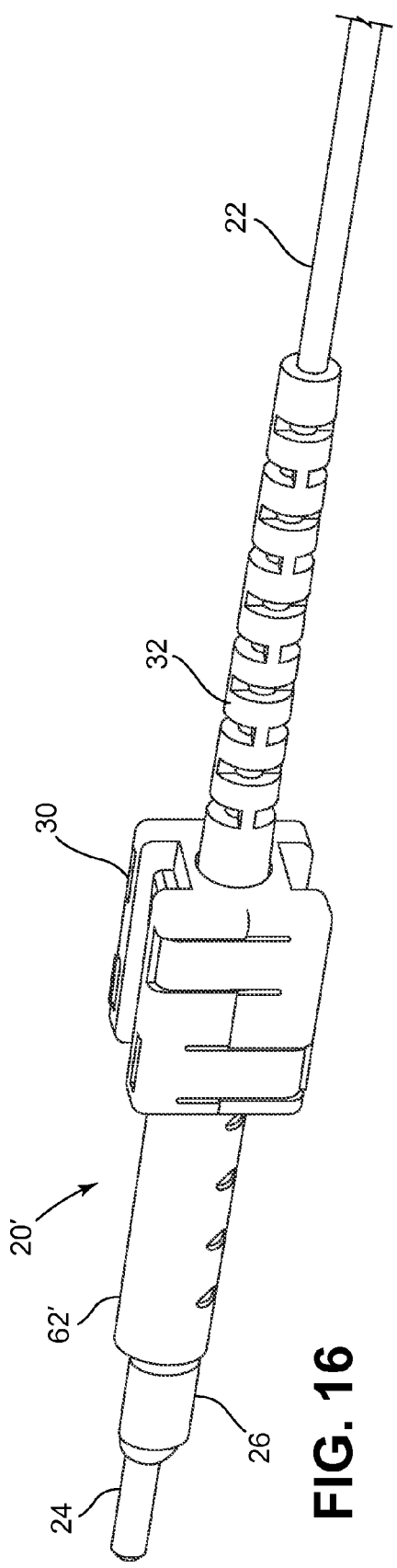

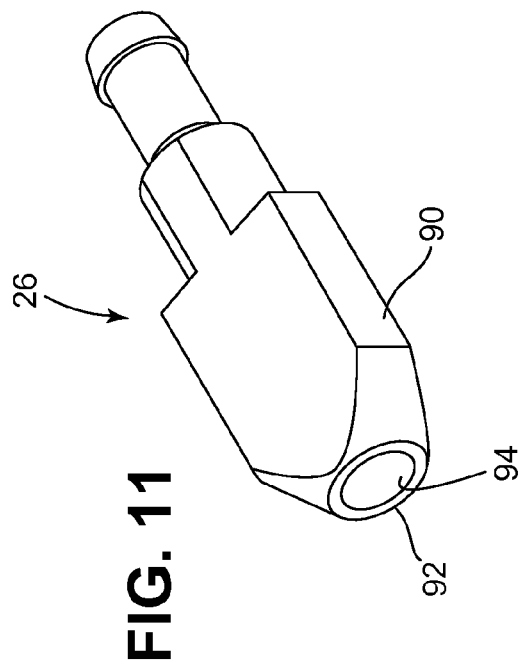
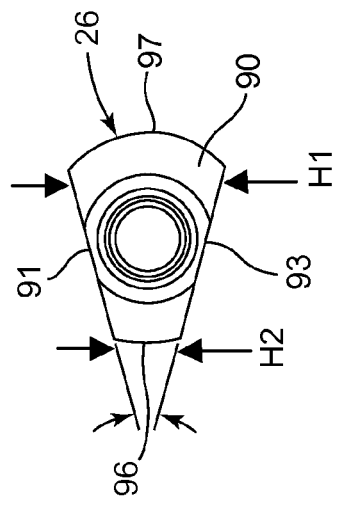
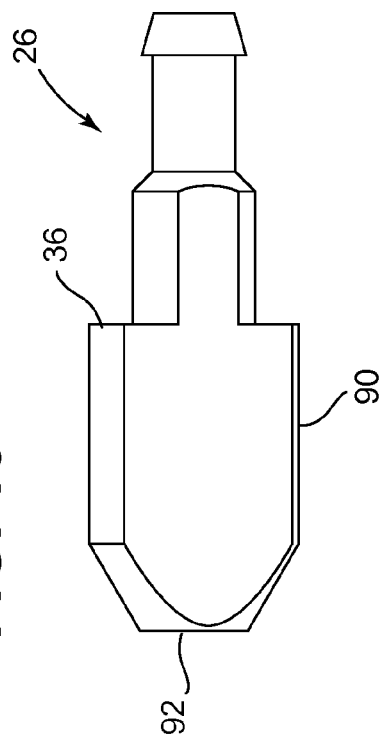
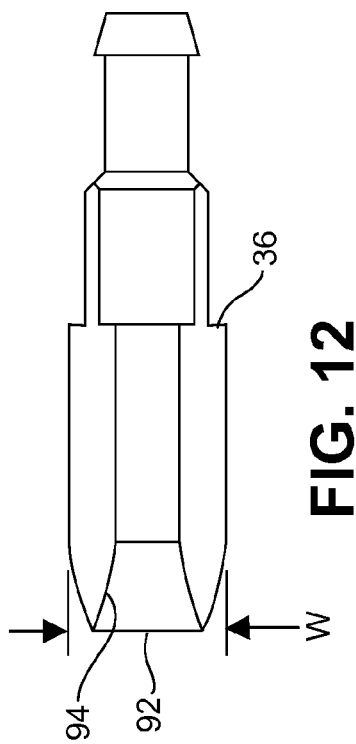
FIG. 11
FIG. 14
FIG. 13
FIG. 12

FIBER OPTIC CONNECTOR WITH FIELD INSTALLABLE OUTER CONNECTOR HOUSING AND KEYED FERRULE HUB

CROSS-REFERENCE TO RELATED APPLICATION

This application is a continuation of application Ser. No. 14/091,984, filed Nov. 27, 2013, which will issue as U.S. Pat. No. 9,182,567, which application claims the benefit of provisional application Ser. No. 61/731,838, filed Nov. 30, 2012, which applications are incorporated herein by reference in their entirety.

TECHNICAL FIELD

The present disclosure relates generally to devices used in optical fiber communication systems. More particularly, the present disclosure relates to fiber optic connectors used in optical fiber communication systems.

BACKGROUND

Fiber optic communication systems are becoming prevalent in part because service providers want to deliver high bandwidth communication capabilities (e.g., data invoice) to customers. Fiber optic communication systems employ a network of fiber optic cables to transmit large volumes of data invoice signals over relatively long distances. Optical fiber connectors are an important part of most fiber optic communication systems. Fiber optic connectors allow two optical fibers to be quickly, optically connected without requiring a splice. Fiber optic connectors can be used to optically interconnect two lengths of optical fiber. Optical fiber connectors can also be used to interconnect lengths of optical fiber to passive and active equipment.

A typical fiber optic connector includes a ferrule assembly supported at a distal end of a connector housing. A spring may be used to bias the ferrule assembly in a distal direction relative to the connector housing. The ferrule functions to support an end portion of at least one optical fiber. In the case of a multi-fiber ferrule, the ends of multiple fibers are supported. The ferrule has a distal end faced at which a polished end of the optical fiber is located. When two fiber optic connectors are interconnected, the distal end faces of the ferrules abut one another. Often, the ferrules are biased together by at least one spring. With the fiber optic connectors connected, their respective optical fibers are coaxially aligned such that the end faces of the optical fibers directly oppose one another. In this way, an optical signal can be transmitted from optical fiber to optical fiber through the aligned end faces of the optical fibers. For many fiber optic connector styles, alignment between two fiber optic connectors is provided through the use of an intermediate fiber optic adapter.

SUMMARY

One aspect of the present disclosure relates to a fiber optic connector having a field installable connector housing assembly. Another aspect of the present disclosure relates to a fiber optic connector system that facilitates installing optical fiber in ducts or other small conduits often found in buildings such as a multiple dwelling units.

A further aspect of the present disclosure relates to a fiber optic connection system where a ferrule is mounted at the end of an optical fiber (e.g., at a factory or other manufacturing center), and a connector housing is field installed at the end of the optical fiber after the optical fiber has been installed at a desired location. For example, the optical fiber can be installed within a conduit, duct or other structure within a building before the connector housing is installed at the end of the optical fiber over the ferrule. In certain examples, a spring and a strain relief boot can be factory installed on the optical fiber. In certain examples, the optical fiber can include a protective buffer layer such as a 900 micron loose or tight buffer tube/jacket. In certain examples, the optical fiber can be incorporated within a cable having an outer jacket and a strength layer (e.g., an aramid yarn strength layer or other layer suitable for providing tensile reinforcement to the optical fiber) positioned between the optical fiber and the outer jacket. In certain examples, the fiber optic cable can have an outer diameter less than 1.5 millimeters or less than 1.4 millimeters or less than 1.3 millimeters, or less than or equal to 1.2 millimeters.

A variety of additional aspects will be set forth in the description that follows. The aspects relate to individual features and to combinations of features. It is to be understood that both the foregoing general description and the following detailed description are exemplary and explanatory only and are not restrictive of the broad inventive concepts upon which the examples disclosed herein are based.

BRIEF DESCRIPTION OF THE DRAWINGS

FIG. 1 is a perspective view of a fiber optic connector in accordance with the principles of the present disclosure;

FIG. 2 is a cross-sectional view of the fiber optic connector of FIG. 1 that bisects the fiber optic connector of FIG. 1 along a vertical plane;

FIG. 7 is a perspective view of a ferrule assembly of the factory installed sub assembly of FIG. 4;

FIG. 8 is another perspective view of the ferrule assembly of FIG. 7;

FIG. 9 is a further perspective view of the ferrule assembly of FIG. 7;

FIG. 11 is a perspective view of a ferrule hub of the ferrule assembly of FIG. 7;

FIG. 12 is a side view of the ferrule hub of FIG. 11;

FIG. 13 is a top view of the ferrule hub of FIG. 11;

FIG. 14 is a front end view of the ferrule hub of FIG. 11;

FIG. 16 shows a portion of a springless fiber optic connector in accordance with the principles of the present disclosure.

DETAILED DESCRIPTION

Figure 3:
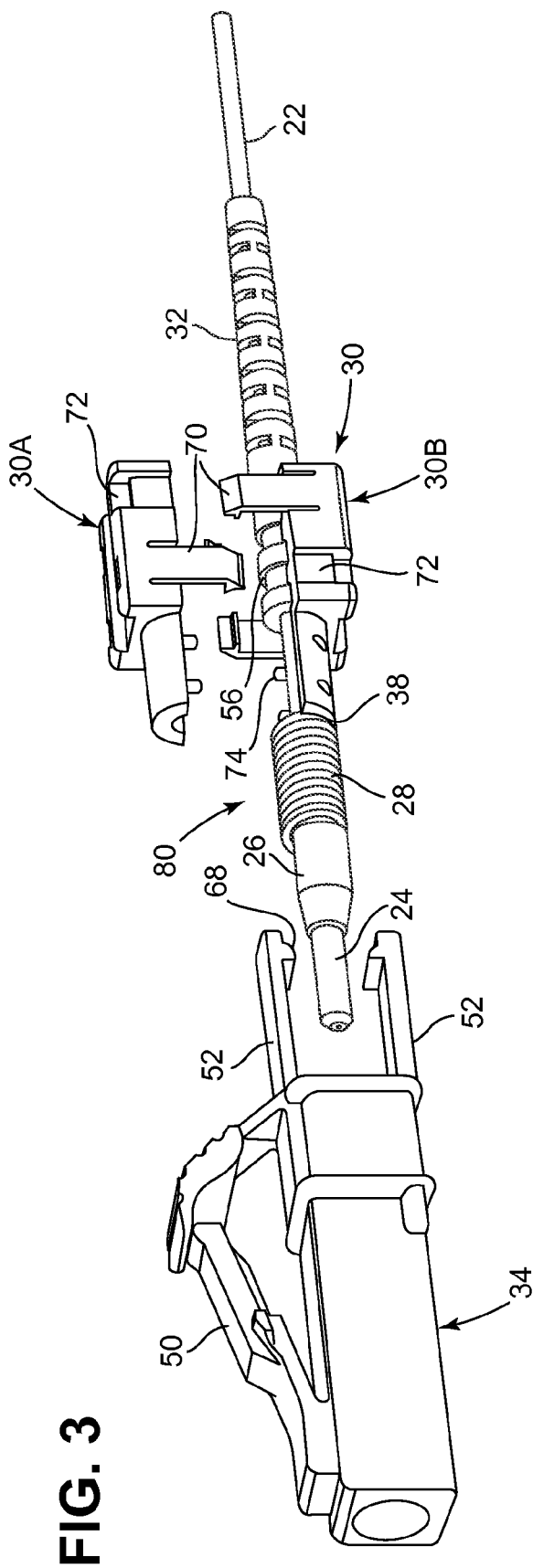
FIG. 3 is an exploded view of the fiber optic connector of FIG. 1.

FIGS. 1-3 illustrate a fiber optic connector 20 in accordance with the principles of the present disclosure. The fiber optic connector 20 is shown installed on an optical fiber 22. As shown at FIG. 3, the fiber optic connector 20 includes a ferrule 24 in which an end portion of the optical fiber 22 is supported, a ferrule hub 26 supporting the ferrule 24, a spring 28, a mounting block 30, a flexible, strain-relief sleeve 32 (e.g., a boot) that provides bend radius protection to the optical fiber 22 and a main connector housing 34. The spring 28 is captured between a backside 36 of the ferrule hub 26 and a front spring stop 38 of the mounting block 30. The mounting block 30 can interlock with the strain relief sleeve 32 to inhibit relative axial movement between the mounting block 30 and the strain relief sleeve 32.

Figure 15:
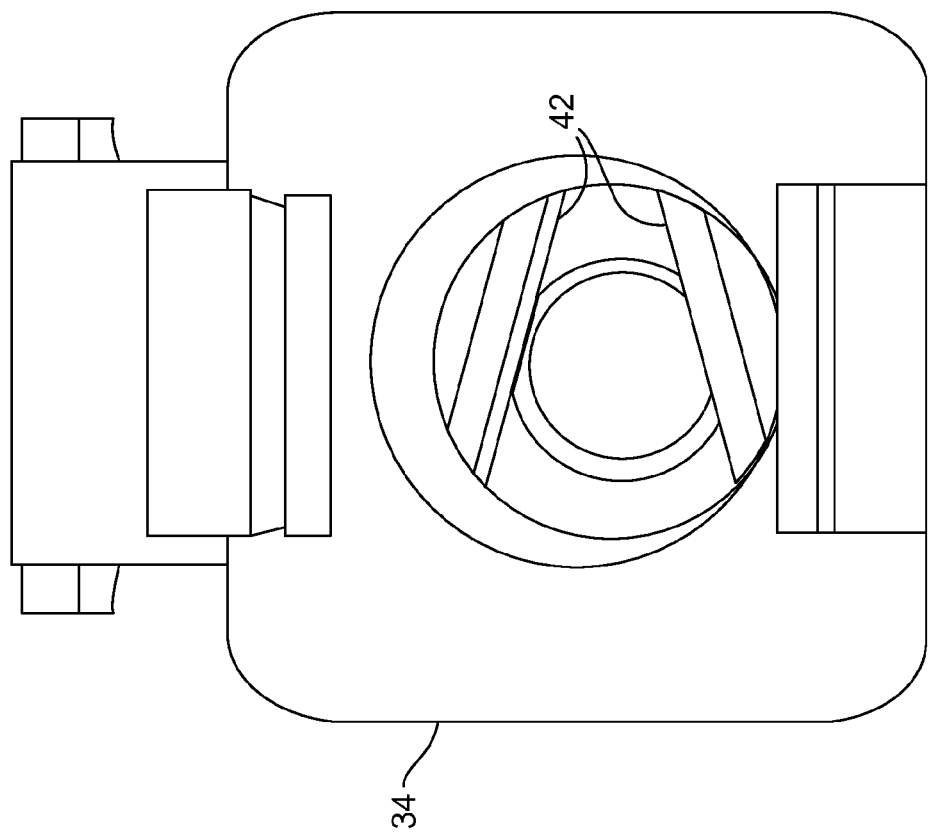
FIG. 15 is a rear view of a main connector housing of the fiber optic connector of FIG. 1.
Figure 10:
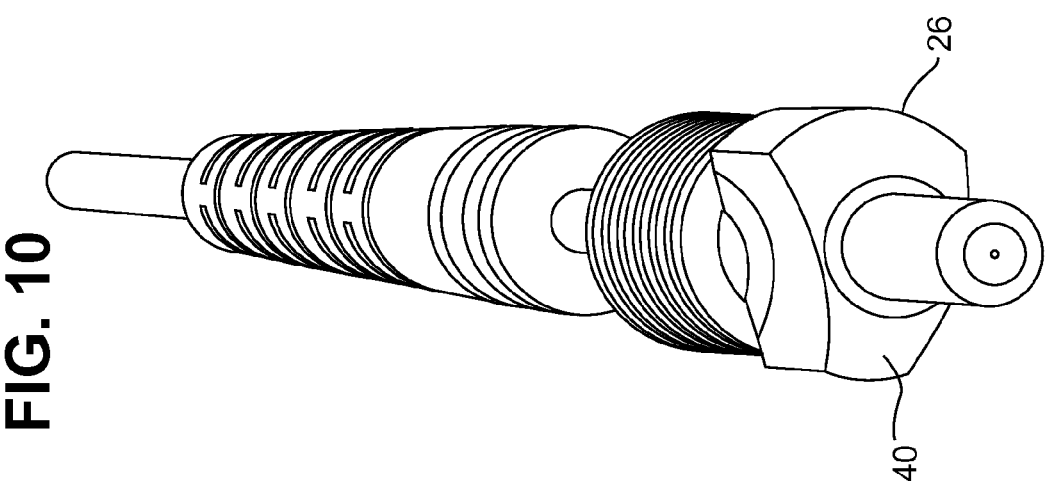
FIG. 10 is still another perspective view of the ferrule assembly of FIG. 7.

The main connector housing 34 forms a front plug portion of the fiber optic connector 20 and is adapted to receive the ferrule 24, the ferrule hub 26, the spring 28 and the front spring stop 38 of the mounting block 30 (see FIG. 2). In certain examples, a keyed relationship is defined between the ferrule hub 26 and the interior of the main connector housing 34 such that the ferrule hub 26 can be inserted into the interior of the main connector housing 34 at only one predetermined rotational orientation (see FIGS. 14 and 15). A front side 40 of the ferrule hub 26 can abut against a shoulder 42 (see FIG. 15) within the main connector housing 34 to stop forward movement of the ferrule hub 26 within the main connector housing 34. The main connector housing 34 can latch or otherwise connect to the mounting block 34 such that the ferrule hub 26 and the spring 28 are captured between the main connector housing 34 and the mounting block 30 and thereby retained within the main connector housing 34 (see FIG. 2).

In certain examples, the spring 28 biases the ferrule hub 26 and the ferrule 24 in a forward direction relative to the main connector housing in 34. In certain examples, a front end face 44 of the ferrule 24 is accessible at a front end 46 of the main connector housing 34. A polished end face of the optical fiber 22 can be located at the front end face 44 of the ferrule 24. In certain examples, the front end face 44 can be angled relative to a longitudinal axis of the optical fiber 22. In other examples, front end face 44 can be perpendicular relative to the longitudinal axis of the optical fiber 22.

In certain examples, the optical fiber 22 includes a core, a cladding layer surrounding the core, one or more coating layers surrounding the cladding layer, and a buffer layer surrounding the one or more coating layers. In certain examples, the core can have an outer diameter in the range of 8-12 microns, the cladding can have an outer diameter in the range of 120-130 microns, the one or more coatings can have an outer diameter in the range of 240-260 microns, and the outer buffer layer can have an outer diameter in the range of 800-1,000 microns. In certain examples, the outer buffer layer can be a loose or tight buffer tube having an outer diameter of about 900 microns. In certain examples, only the core and the cladding of the optical fiber 22 are supported within the ferrule 24.

It will also be appreciated that the core and the cladding can be constructed of a material suitable for conveying an optical signal such a glass (e.g., a silica-based material). The cladding layer can have an index of refraction that is less than the index of refraction of the core. This difference between the index of refraction of the cladding layer and the index of refraction of the core allows an optical signal that is transmitted through the optical fiber to be confined to the core. In certain examples, the optical fiber is a bend insensitive fiber having multiple cladding layers separated by one or more trench layers. The one or more coating layers typically have a polymeric construction such as acrylate.

In certain examples, the optical fiber is incorporated into a fiber optic cable having a strength layer (e.g., a layer of aramid yarn) surrounded by an outer jacket. In certain embodiments, the buffer layer is eliminated and the strength layer directly surrounds the coating layer of the optical fiber.

In certain examples, the fiber optic cable has an outer diameter less than 1.5 millimeters, or less than 1.4 millimeters, or less than 1.3 millimeters, or less than or equal to 1.2 millimeters. For example, some such optical fibers are disclosed in U.S. application Ser. No. 12/473,931, filed May 28, 2009, and titled "FIBER OPTIC CABLE," the disclosure of which is hereby incorporated herein by reference.

The main connector housing 34 of the fiber optic connector 20 forms a plug portion of the fiber optic connector 20 that is configured to fit within a corresponding fiber optic adapter. In the depicted embodiment, the main connector housing 34 is an LC-type connector housing configured to fit within an LC-type fiber optic adapter. The main connector housing 34 includes a front latch 50 for securing the main connector housing 34 within the fiber optic adapter. The main connector housing 34 also includes rear latches 52 (FIG. 3) that latch to the mounting block 34 for providing a snap-fit connection between the main connector housing 34 and the mounting block 30 (see FIG. 2). Once the main connector housing 34 and the mounting block 30 are latched together, relative axial movement between the main connector housing 34 and the mounting block 30 along the longitudinal axis of the optical fiber 22 is limited or prevented. In certain examples, the rear latches 52 can be flexed apart to disengage the main connector housing 34 from the mounting block 30 for repair, re-assembly, cleaning, or other reasons. In other examples, the main connector housing 34 can correspond to other connector types, such as SC-type connectors, ST-type connectors, FC-type connectors, or other types of connectors.

The strain relief sleeve 32 is elongated and has a central opening for receiving the optical fiber 22. In certain examples, the strain relief sleeve 32 has a polymeric construction and is flexible. In certain examples, the strain relief sleeve 32 has a tapered construction that reduces in cross-sectional size as the strain relief sleeve 32 extends rearwardly from the mounting block 30. In certain examples, the strain relief sleeve 32 can have a segmented construction that enhances flexibility (see FIG. 2). As shown at FIG. 3, a forward end portion of the strain relief sleeve 32 defines two axially spaced apart circumferential grooves 56 that receive corresponding circumferential ribs defined within the mounting block 30 (see FIG. 3) to provide a mechanical interlock between the strain relief sleeve 32 and the mounting block 30. The mechanical interlock inhibits or prevents relative axial movement between the strain relief sleeve 32 and the mounting block 30. In this way, the strain relief sleeve 32 is locked in place relative to the mounting block 30 when the mounting block 30 is mounted over the strain relief sleeve 32.

Figure 6:
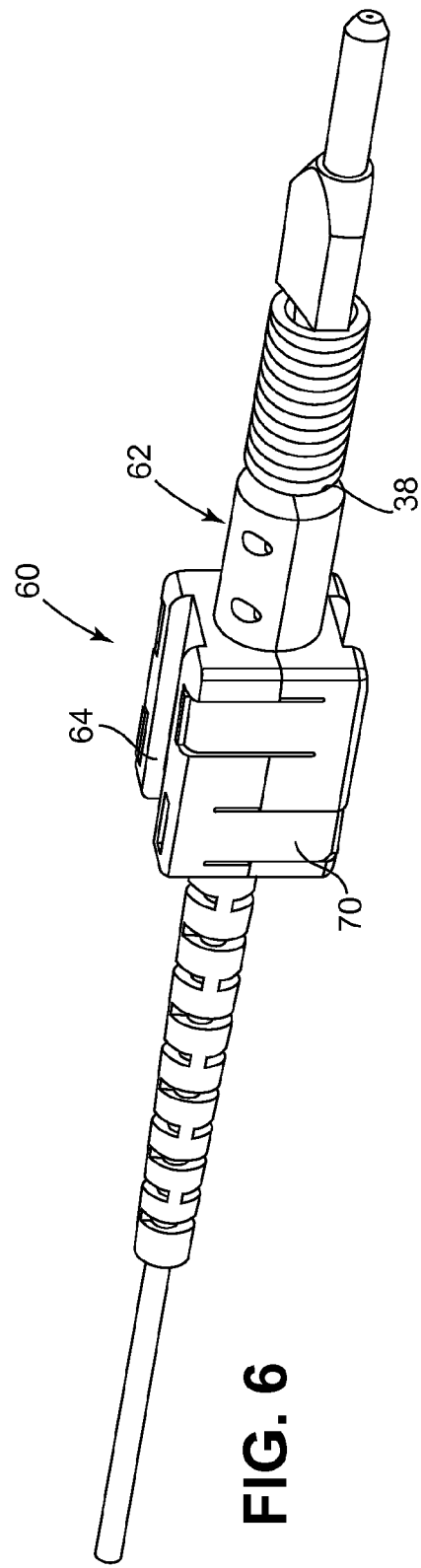
FIG. 6 illustrates a second step for installing the field installable connector housing assembly on the factory installed sub assembly of FIG. 4.

Referring to FIG. 6, the mounting block 30 has a generally rectangular main body 60 and a front extension 62 that projects forwardly from the main body 60. A front end of the front extension 62 forms the front spring stop 38. The main body 60 includes top and bottom axial slots 64 that receive the rear latches 52 of the main connector housing 34. The main body 60 also defines retention shoulder 66 adjacent a rear end of the main body 60. Catches 68 of the rear latches 52 of the main connector housing 34 engage the retention shoulder 66 to provide the snap-fit connection between the main connector housing 34 and the mounting block 30.

As shown at FIG. 3, the mounting block 30 includes a two-piece construction including an upper piece 30A and a lower piece 30B that can be fastened together by a snap-fit connection provided by latches 70. As indicated above, axially spaced-apart ribs can be provided within the main body 60 to provide the interlock between the main body 60 and the strain relief sleeve 32. By positioning the top and bottom pieces 30A, 30B of the mounting block 30 so that the axial ribs align with the circumferential grooves 56 of the strain relief sleeve 32, and then snapping the top and bottom pieces 30A, 30B together around the strain relief sleeve 32, the mounting block 30 and the strain relief 32 are effectively interlocked together.

Figure 5:
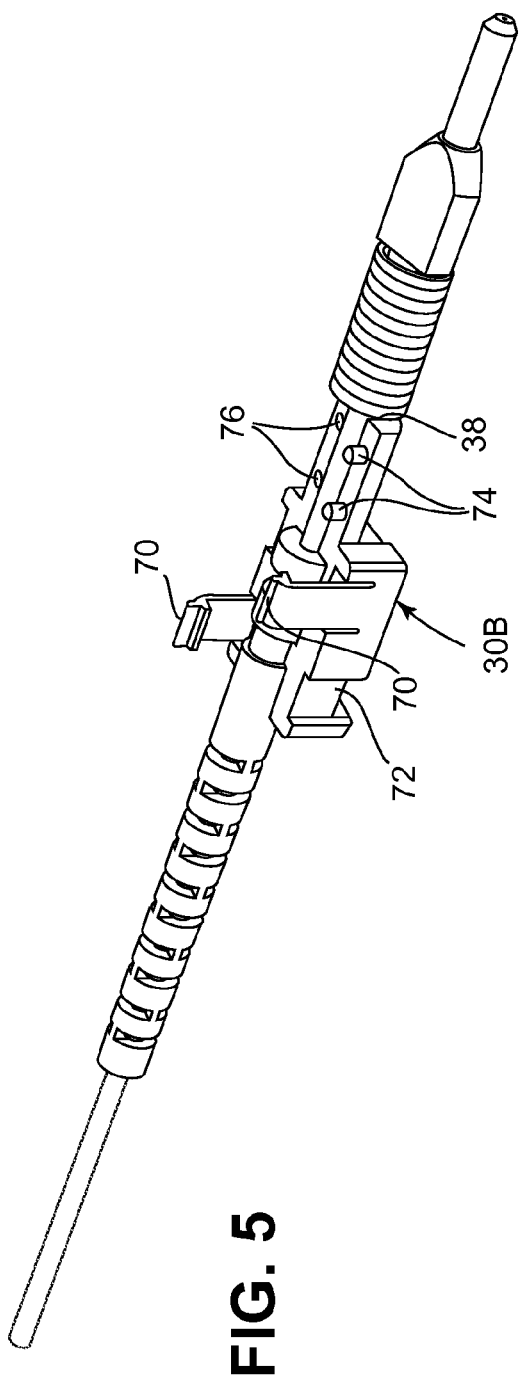
FIG. 5 illustrates a first step for installing a field installable connector housing assembly on the factory installed sub assembly of FIG. 4.

The top and bottom pieces 30A, 30B of the mounting block 30 can include mating pins 74 and openings 76 provided at the front extension 62 at the interface between the top and bottom pieces 30A, 30B (see FIG. 5). The mating pins 74 and openings 76 assist in maintaining alignment between the top and bottom pieces 30A, 30B of the mounting block 30.

Figure 4:
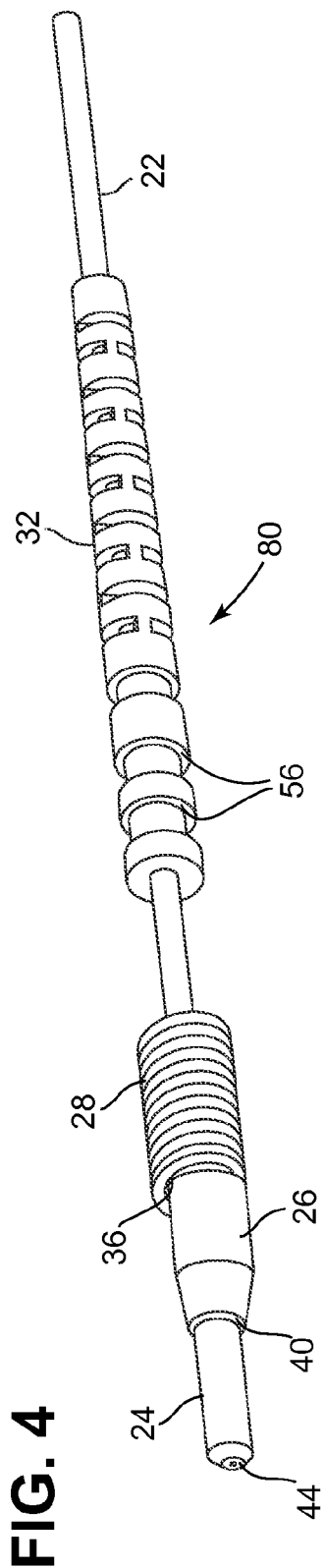
FIG. 4 is a perspective view of a factory-installed sub-assembly of the fiber optic connector of FIG. 1.

The ferrule 24, the ferrule hub 26, the spring 28, and the strain relief sleeve 32 can form a first sub-assembly 80 (see FIG. 4) of the fiber optic connector 20. In certain examples, the first sub-assembly can be factory installed on the optical fiber 22. Similarly, the front end face 46 of the optical fiber 22 can be factory processed (e.g., polished). In certain examples, the strain relief sleeve 32 and the spring 28 can be slid over the optical fiber 22 in the factory. Thereafter, the ferrule 24 and the ferrule hub 26 can be mounted at the end of the optical fiber 22 and the end faces of the optical fiber 22 and the ferrule 24 can be processed in a factory setting.

In certain examples, the ferrule 24 can be mounted in the ferrule hub 26 such that a rotational position of a core offset of the optical fiber 22 relative to the ferrule 24 is set at predetermined rotational position relative to the ferrule hub 26. This core offset provides tuning of the connector. The term "core offset" refers to a direction in which the core is offset from being perfectly concentric with the ferrule 24. In certain examples, the end face of the ferrule 24 can be polished at an angle, and the ferrule 24 can be mounted in the ferrule hub 26 such that the angle can be set at a desired rotational orientation relative to the ferrule hub 26 in the factory. Providing a keyed relationship between the ferrule hub 26 and the main connector housing 34, combined with establishing a predetermined rotational relationship between the ferrule hub 26 and the angle or core concentricity of the ferrule end face 44, enables the angle of the end face or the core concentricity to be set at a predetermined rotational orientation relative to the main connector housing 34.

Referring to FIGS. 7, 8, and 11-14, the ferrule hub 26 defines a central opening for receiving the optical fiber 22. The ferrule hub 26 includes a main body 90 having a front end 92 defining a receptacle 94 for receiving a rear end of the ferrule 24. As shown at FIG. 14, the main body 90 has opposite top and bottom major sides 91, 93 that are angled relative to one another. As shown at FIG. 14, the top and bottom major sides 91, 93 extend across a width W of the main body 90. The width W extends between left and right sides 96, 97 of the main body 90. The right side 97 has a height H1 that is larger than a height H2 defined at the left side 96 of the main body 90. This difference in height is provided by the taper angle between the top and bottom major sides 91, 93. It will be appreciated that the shape of the main body 90 compliments a corresponding shape of a pocket 100 defined within the interior of the main connector housing 34. The complimentary shape between the main body 90 and the pocket 100 (see FIG. 15) ensures that the ferrule hub 26 can be inserted into the main connector housing 34 in only one rotational position. The single rotational position is dictated by the angled top and bottom surfaces 91, 93 and corresponding angled top and bottom surfaces 101, 103 of the pocket 100 within the main connector housing 34.

Referring back to FIGS. 1 and 3, the mounting block 30 and the main connector housing 34 can form a second sub-assembly 110. In certain examples, the second sub assembly 110 can be installed over the first sub-assembly 80 in the field (see FIG. 3). For example, the first sub-assembly 80 can be factory installed on the optical fiber 22. The optical fiber 22 with the first sub-assembly 80 installed thereon can then be delivered to a field location. One example field location is a multi-dwelling unit or other building. The optical fiber 22 with the first sub-assembly 80 mounted thereon can then be installed at the field location. For example, the optical fiber 22 with the first sub-assembly 80 mounted thereon can be routed along one or more routing paths that may extend through structures, such as ducts, risers, plenums, or other passages. The relatively small cross-sectional profile of the first sub-assembly 80 allows the optical fiber 22 with the first sub-assembly 80 mounted thereon to be easily routed along the desired routing path even in situations where the optical fiber 22 is routed through ducts having relatively small internal passages. The small cross-sectional profile also allows multiple optical fibers 22 to be incorporated into a carrier (e.g., a sleeve, tube, pulling sock, jacket, etc.) having a small form factor.

When the end of the optical fiber 22 with the first sub-assembly 80 mounted thereon has been routed to a desired position at the field location, the mounting block 30 can be snapped over the strain relief sleeve 32; and the ferrule 22, the ferrule hub 26, and the spring 28 can be inserted into the backside of the main connector housing 34. The main connector housing 34 is then latched to the mounting block 30 and the fiber optic connector 20 is fully assembled. Thereafter, the fiber optic connector 20 can be used in the same way as a standard type of connector. For certain applications, it will be appreciated that the spring 28 may be optional. In this regard, FIG. 16 shows an alternative connector 20' where the spring 28 has been eliminated and a front extension 62' of the mounting block 30 has been extended to fill the space that would typically be occupied by the spring 28.

What is claimed is:

1. A connectorized optical fiber cable comprising:
  an optical fiber having a first end defining a polished end face;
  a ferrule arrangement holding the first end of the optical fiber so that the polished end face is accessible from an exterior of the ferrule arrangement, the ferrule arrangement having a keyed portion; and
  a connector housing arrangement extending from a front to a rear, the connector housing arrangement carrying the ferrule arrangement so that the ferrule arrangement is axially movable relative to the connector housing arrangement, the connector housing arrangement having an interior defining a pocket such that the keyed portion of the ferrule arrangement fits in the pocket in only one rotational orientation, the polished end face of the optical fiber being accessible at the first end of the connector housing, the optical fiber extending outwardly from the second end of the connector housing.

2. The connectorized optical fiber cable of claim 1, further comprising a spring disposed within the connector housing arrangement to provide a forward bias to the ferrule arrangement relative to the connector housing arrangement.

3. The connectorized optical fiber cable of claim 1, wherein the connector housing arrangement includes a forward member and a rearward member, the forward member limiting forward movement of the polished end face, and the rearward member limiting rearward movement of the polished end face.

4. The connectorized optical fiber cable of claim 3, wherein the forward member defines a plug portion.

5. The connectorized optical fiber cable of claim 3, wherein the rearward member is disposed within the forward member.

6. The connectorized optical fiber cable of claim 3, further comprising a strain relief member coupled to the rearward member in an axially fixed configuration.

7. The connectorized optical fiber cable of claim 1, wherein the connector housing arrangement defines an LC-type connector housing.

8. The connectorized optical fiber cable of claim 1, wherein the keyed portion of the ferrule arrangement is keyed to indicate a core concentricity of the polished end face of the optical fiber.

9. The connectorized optical fiber cable of claim 1, wherein the keyed portion of the ferrule arrangement includes a main body having first and second major surfaces that are angled relative to one another.

10. The connectorized optical fiber cable of claim 9, wherein the keyed portion also includes a first curved sidewall extending between first sides of the first and second major surfaces.

11. The connectorized optical fiber cable of claim 10, wherein the keyed portion also includes a second curved sidewall extending between second sides of the first and second major surfaces.

12. The connectorized optical fiber cable of claim 11, wherein the second curved sidewall is longer than the first curved sidewall.

13. The connectorized optical fiber cable of claim 1, further comprising a strain relief member coupled to the second end of the connector housing arrangement, the strain relief member providing strain relief to the optical fiber.

14. The connectorized optical fiber cable of claim 13, wherein the strain relief is coupled to a rearward member of the connector housing arrangement.

15. The connectorized optical fiber cable of claim 13, wherein the strain relief member defines two axially spaced apart circumferential grooves that receive corresponding circumferential ribs defined by the rearward member.

16. A method of connectorizing a first end of an optical fiber, the method comprising:
mounting an optical fiber to a ferrule arrangement such that a rotational position of a core offset of the optical fiber relative to the ferrule arrangement is set at predetermined rotational position relative to the ferrule arrangement;
rotationally aligning the ferrule arrangement with a keyed cavity of a plug housing, wherein the ferrule arrangement rotationally aligns with the keyed cavity in only one rotational orientation; and
inserting the aligned ferrule arrangement into the keyed cavity of plug housing from a rear of the plug housing so that a polished end of the optical fiber is accessible from a front of the plug housing.

17. The method of claim 16, wherein inserting the aligned ferrule arrangement into the keyed cavity includes inserting a spring within the plug housing so that the spring biases the ferrule arrangement forwardly.

18. The method of claim 16, further comprising inserting a mounting block into the rear of the plug housing after inserting the aligned ferrule arrangement, thereby holding the aligned ferrule arrangement within the plug housing.

19. The method of claim 18, wherein the mounting block is latched to the plug housing.

20. The method of claim 18, further comprising interlocking a strain relief member with the mounting block.

* * * * *